United States Patent [19]

Naser

[11] Patent Number: 5,653,766

[45] Date of Patent: Aug. 5, 1997

[54] POST-OPERATIVE PROSTHETIC DEVICE

[75] Inventor: Aziz Naser, Canton, Mich.

[73] Assignee: Michigan Orthopedic Services, LLC, Livonia, Mich.

[21] Appl. No.: 605,906

[22] Filed: Feb. 23, 1996

[51] Int. Cl.$^6$ ........................................................ A61F 2/80
[52] U.S. Cl. ............................... 623/33; 623/32; 623/36; 602/23; 602/62
[58] Field of Search ...................... 623/33–38, 32; 602/23, 62

[56] References Cited

U.S. PATENT DOCUMENTS

| | | |
|---|---|---|
| 2,908,016 | 11/1959 | Botko . |
| 3,545,009 | 12/1970 | Colley . |
| 4,274,166 | 6/1981 | Chambers . |
| 4,409,972 | 10/1983 | Prahl . |
| 4,634,446 | 1/1987 | Kristinsson . |
| 4,842,608 | 6/1989 | Marx et al. .................. 623/33 |
| 4,872,879 | 10/1989 | Shamp ........................... 623/36 |
| 4,955,920 | 9/1990 | Wellershaus et al. . |
| 4,988,360 | 1/1991 | Shamp ........................... 623/33 |
| 5,007,937 | 4/1991 | Fishman et al. . |
| 5,108,455 | 4/1992 | Telikicherla . |
| 5,139,523 | 8/1992 | Paton et al. . |
| 5,314,497 | 5/1994 | Fay et al. . |
| 5,376,129 | 12/1994 | Faulkner et al. . |
| 5,507,722 | 4/1996 | Richardson ................... 623/33 |

FOREIGN PATENT DOCUMENTS

| | | | |
|---|---|---|---|
| 2103490 | 2/1983 | United Kingdom ....................... 623/33 |
| 9503760 | 2/1995 | WIPO .......................... 623/33 |

OTHER PUBLICATIONS

Orthomedics Product Brochure; pp. 8–1, 8–2, 8–3.
PEL Product Brochure; pp. 104, 106.
West Coast Brace & Limb Product Brochure; pp. 65, 67.

Primary Examiner—John G. Weiss
Assistant Examiner—Bruce E. Snow
Attorney, Agent, or Firm—Howard & Howard

[57] ABSTRACT

A prosthetic device for use in rehabilitating a patient after a limb reduction surgery, allows the patient to begin learning to walk with a bendable knee joint that is typically used with a more permanent, later provided prosthetic. The inventive prosthetic device includes an adjustable first portion that is secured about a portion of the amputated limb and a second portion that provides axial and radial clearance between the terminal end of the amputated limb and the interior of the prosthetic sleeve. The second portion of the prosthetic sleeve also includes a radially defined opening that assists a patient or medical personnel in observing the terminal end of the amputated limb during the post-operative healing process.

20 Claims, 1 Drawing Sheet

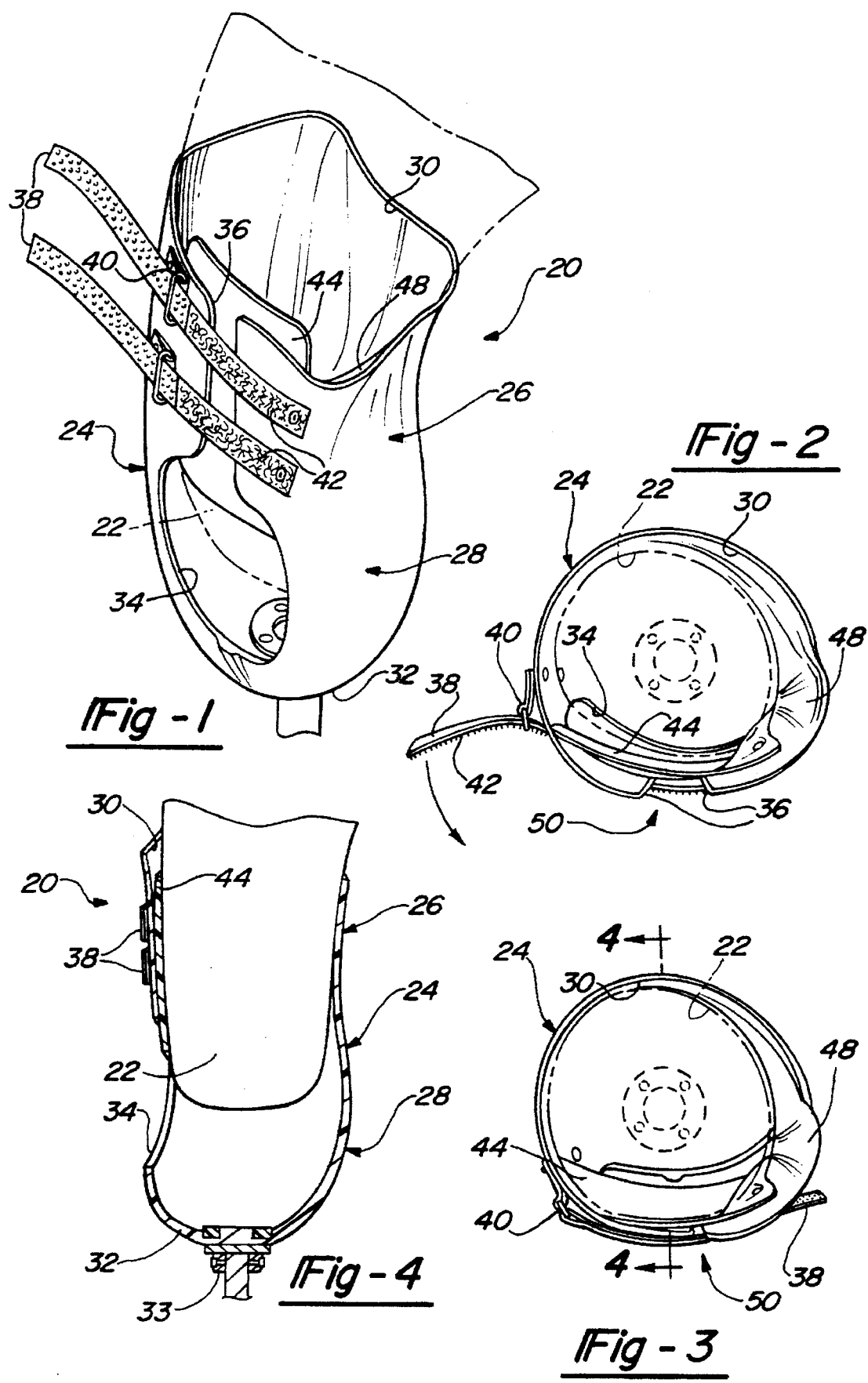

POST-OPERATIVE PROSTHETIC DEVICE

BACKGROUND OF THE INVENTION

This invention relates generally to prosthetic devices and, more specifically, to a prosthetic device for use immediately after a limb reduction surgery until the patient is fitted with a more permanent prosthesis.

Medical and technological inventions have provided significantly enhanced prosthetic devices for patients that have had limb reduction surgery. There is still a need, however, for a more effective immediate post-operative prosthesis that can be used by patients that have had an above-the-knee amputation surgery. Typically, after an above-the-knee amputation surgery, the patient is fitted with an immediate post-operative prosthesis that the patient uses to begin to learn to walk with the newly amputated limb.

A significant disadvantage associated with conventional immediate post-operative prosthetic devices is that they are functionally different from the more permanent prosthesis later provided to the patient. Conventional immediate post-operative prosthetic devices for above-the-knee amputation patients do not have a bendable knee joint, whereas permanent prosthetics have bendable knee joints. Therefore, shortly after surgery the patient begins to learn to walk with the reduced limb using a prosthetic device that is not the same as the patient will be provided on a more permanent basis at a later time. This presents certain difficulties including a tendency for the patient to develop an unnatural walking pattern or gait that can cause undue strain on the patient's hip joint. Further, the patient typically has to "re-learn" to walk with later-provided prosthetic devices, which include a temporary and definitive prosthetic that have a bendable knee joint.

Prior to this invention only the temporary and definitive prosthetics were provided with bendable knee joints. A more permanent prosthetic cannot be used in a post-operative setting because design criteria are different. For example, permanent prosthetics ideally provide total contact between the reduced limb and the prosthetic. Conversely, an immediate post-operative prosthetic preferably avoids contact between the end of the reduced limb and the prosthetic. Shortly after surgery, Edema is presented, the point of amputation is extremely sensitive and any contact with a prosthetic while walking would cause the patient to experience discomfort and could interfere with the healing process. Additionally, such contact could cause the suture line to separate causing undesirable drainage, which lengthens the healing process.

Accordingly, it is desirable to provide an immediate post-operative prosthetic device that is adaptable to be used with a bendable knee joint. This provides significant advantages in that the patient learns to walk with a more normal gait during rehabilitation immediately after the surgery, which avoids the patient developing bad gait patterns such as hip hiking, vaulting, or circumducting of the hip joint or prothesis. Accordingly, the risk of the patient developing a walking pattern that causes undue strain on the hip joint is reduced.

SUMMARY OF THE INVENTION

In general terms, this invention is a prosthetic device for use after limb reduction surgery that includes a generally cylindrical sleeve having an axial opening at a first end for receiving an amputated limb. The generally cylindrical sleeve is closed at a second axial end, which is adapted to be connected to a bendable knee joint. The cylindrical sleeve has a first portion extending from the first end toward a longitudinal midsection of the sleeve. The first portion has a first inner surface circumference. The sleeve also has a second portion extending between the first portion and the second end. The second portion has a second inner surface circumference that is greater than the first inner surface circumference so that the amputated limb contacts only the first inner surface and the terminal end of the amputated limb does not contact the second inner surface of the second portion.

In another embodiment, the first portion includes a longitudinal split extending along the length of the first portion. An adjustment member is provided for adjusting the spacing defined by the longitudinal split such that the first inner surface circumference of the first portion is adjustable. The second portion of the sleeve also includes a radially defined opening for viewing at least the terminal end on the amputated limb without removing the limb from the sleeve.

In the most preferred embodiment, the longitudinal split on the first portion extends between the axial opening at the first end of the sleeve and the radially defined opening in the second portion of the sleeve.

These and other features and advantages of a prosthetic device designed according to this invention will become apparent to those skilled in the art from the following detailed description of a preferred embodiment. The drawings that accompany the detailed description can be briefly described as follows.

BRIEF DESCRIPTION OF THE DRAWINGS

FIG. 1 is a perspective view of a post-operative prosthetic device for use by an above-the-knee amputee designed according to this invention.

FIG. 2 is a top elevational view of the embodiment of FIG. 1.

FIG. 3 is a top elevational view of the embodiment of FIG. 2 in an adjusted position.

FIG. 4 is a cross-sectional view taken along the lines 4—4 of FIG. 3.

DETAILED DESCRIPTION OF THE PREFERRED EMBODIMENT

FIG. 1 is a perspective illustration of an immediate post-operative prosthetic device 20 for use with an amputated limb 22. The illustrated device is particularly adapted for a patient that has undergone a limb reduction surgery resulting in an above-the-knee amputation. The prosthetic device 20 includes a sleeve 24 that is at least partially received about the limb 22. The sleeve 24 is preferably made of a copolymer plastic, plastic polypropylene or a polyester resin. In one preferred embodiment, the sleeve 24 is vacuum formed. It is also possible to use a conventional thermo-forming process by heating the plastic material and forming it over a mold.

The sleeve 24 includes a first portion 26 and a second portion 28. An axial opening 30 allows the sleeve 24 to be received about a portion of the limb 22. The axial end of the sleeve 24 that is opposite from the axial opening 30 is closed at 32. The end 32 is adapted to be connected to a conventional, bendable knee joint (partially illustrated diagrammatically at 33). Prior to this invention, it was not possible to provide a patient with an immediate post-operative prosthetic that includes a bendable knee joint that is the same (or essentially the same) as a knee joint that later will be included in a more permanent prosthetic.

The second portion 28 of the sleeve 24 includes a radially defined opening 34. The radially defined opening 34 provides the significant advantage of allowing the patient or medical personnel to observe the terminal end of the limb 22, which would include the suture point at the point of limb reduction. This enables the patient or medical personnel to determine whether drainage has occurred and the dressing on the reduced limb 22 need be changed, for example, without removing the limb 22 from the sleeve 24. The opening 34 also allows one to visually observe any undesirable contact between the limb and sleeve which can cause undue pressure on the suture line.

As best illustrated in FIGS. 1 and 4, the interior volume of the second portion 28 is great enough such that an axial and radial clearance exists between the terminal end of the limb 22 and the inner surface of the second portion 28. It is important to maintain clearance between the end of the amputated limb 22 and the prosthetic device because the end of the limb is typically sore, edemous and not healed sufficiently shortly after surgery. Moreover, contact between the end of the limb 22 and the interior of a prosthetic device while the patient is learning to walk shortly after surgery can cause complications in the healing process.

The first portion 26 preferably includes a longitudinal slit 36. The longitudinal slit 36 preferably extends along the length of the first portion 26 between the axial opening 30 and the radially defined opening 34. The longitudinal slit 36 enables an inner surface circumference of the first portion 26 to be adjusted. Therefore, the sleeve 24 can be comfortably and securely adjusted about a portion of the amputated limb 22. The adjustability permits weight bearing on the ischial tuberosity and circumferentially around the middle to upper portion of the amputated limb.

The first portion of the sleeve 24 is preferably generally flexible in a radial direction such that the circumference of the first portion 26 can be adjusted by flexing the first portion 26 in order to adjust the length of an arcuate gap defined by the longitudinal slit 36. The first portion 26 should also be substantially rigid in an axial direction because the prosthetic device 20 assists in supporting the patient as the patient learns to walk with the reduced limb 22. The second portion 28 of the sleeve 24 is preferably substantially rigid in an axial and radial direction to provide stable support and to avoid contact between the end of the reduced limb and the second portion 28. Therefore, the sleeve 24 can be described as self-supporting.

After the limb 22 is inserted through the axial opening 30, the size of the gap 36 is adjusted using adjustment members 38. Adjustment members 38 are preferably straps mounted onto the sleeve 24 by conventional hinges or clasps 40 that allow the effective length of the straps 38 to be adjusted. In the most preferred embodiment, the straps 38 include the adjustable hook and loop fabric weave known as Velcro™ so that the effective length of the straps 38 can be infinitely adjusted within a given range. A foam pad or flap 44 is provided that extends across the slit 36 in order to enhance patient comfort and to avoid the gathering of the patient's skin within the split 36. FIGS. 2 and 3 illustrate that straps 38 are used to adjust the arcuate length of a gap 50 defined by the split 36. FIG. 2, for example, illustrates a gap 50 when the sleeve 24 is first placed about the limb 22. FIG. 3 illustrates the first portion 26 of the sleeve 24 secured about the limb 22 so that the patient can walk with the help of the prosthetic device 20. FIG. 3 illustrates the reduced arcuate length of the gap 50 after the straps 38 were used to tighten the first portion 26 about the limb 22.

Once the limb 22 is properly received within the sleeve 24 and the straps 38 are appropriately adjusted so that a secure fit is achieved between the first portion 26 and a portion of the limb 22, a conventional waste belt or silesian belt is used to fully secure the prosthetic 20 to the patient. The patient then is able to walk using the prosthetic device 20.

The prosthetic device 20 includes an ischial shelf or seat 48. The ischial seat 48 is preferably formed near the upper medial and posterior edge of the sleeve 24. The seat 48 bears against the ischial tuberosity as the patient stands or walks while wearing the prosthetic device 20.

The foregoing description is exemplary rather than limiting in nature. Variations and modifications of the described embodiment are possible that do not depart from the purview and spirit of this invention. For example, the radially defined opening 34 and the split 36 are illustrated on the anterior side of the sleeve 24. It is also possible to have the opening 34 and the split 36 on a medial or lateral side of the sleeve 24. Accordingly, the scope of this invention is to be limited only by the appended claims.

What is claimed is:

1. A prosthetic device for use after an above-the-knee limb reduction surgery, comprising:

a generally cylindrical sleeve having an axial opening at a first end for receiving an amputated limb and being closed at a second axial end, said closed second end providing a load bearing surface, which is adapted to be connected to a bendable knee joint, said first end including a load bearing shelf portion adapted to bear against an ischial bone on a wearer of said device;

said sleeve having a first portion extending from said first end toward a longitudinal midsection of said sleeve, said first portion having an adjustable first inner surface circumference;

said sleeve having a second portion extending between said first portion and said second end, said second portion having a fixed second inner surface circumference that is larger than said first circumference such that upon insertion the amputated limb contacts only said first inner surface and a terminal end of the amputated limb does not contact said second inner surface of said second portion, said second portion including a radially defined opening for viewing a portion of the amputated limb from outside said sleeve without removing the amputated limb from said sleeve.

2. The device of claim 1, wherein said first portion includes a longitudinal split extending along said first portion.

3. The device of claim 2, further comprising an adjusting member for adjusting said first circumference such that said first portion remains in selected contact with a portion of the amputated limb.

4. The device of claim 3, wherein said adjusting member comprises two straps having an adjustable length, said straps being selectively maintained at a selected length to maintain said first circumference at a fixed length.

5. The device of claim 3, further comprising a flap disposed within said sleeve and extending across said split.

6. The device of claim 1, wherein said sleeve is formed of a copolymer substance such that said first portion is generally radially flexible and axially rigid and said second portion is radially and axially rigid.

7. The device of claim 1, wherein said second portion is generally spherical.

8. A prosthetic device for use after an above-the-knee limb reduction surgery comprising:

a generally cylindrical sleeve having an axial opening at a first end for receiving an amputated limb and being closed at a second end distal from said axial opening, said second end providing a weight bearing surface;

a fixture supported on said second end that is adapted to be connected to a bendable knee joint;

said sleeve having a first portion extending from said axial opening toward a longitudinal midsection of said sleeve;

an adjustment member for adjusting a circumferential dimension of said first portion; and wherein said sleeve includes a second portion extending between said first portion and said second end, said second portion having a radially defined opening for viewing at least a terminal end on the amputated limb without removing the limb from said sleeve, said first portion including a longitudinal split extending between said axial opening and said radially defined opening.

9. The device of claim 8, wherein said second portion has an inner surface dimensioned such that the terminal end of the amputated limb does not contact any portion of said inner surface.

10. The device of claim 8, wherein said first portion has an inner surface circumference that is adjustable between a largest circumference and a smallest circumference by adjusting a spacing defined by said longitudinal split and wherein said second portion has an inner surface circumference that is greater than said largest first inner circumference.

11. The device of claim 8, wherein said sleeve is formed from a copolymer substance such that said first portion is generally flexible in a radial direction and substantially rigid in an axial direction and such that said second portion is substantially rigid in radial and axial directions.

12. A temporary prosthetic device for use after an amputation surgery, comprising:

a generally cylindrical sleeve having a length and an axial opening at a first end for receiving an amputated limb and being axially closed at a second end distal from said axial opening, said second end providing a load bearing surface such that an axial load placed on said second end is distributed along the length of said sleeve, said sleeve being substantially rigid along an entirety of said length;

said sleeve having a first portion adapted to be secured about a portion of the limb and extending from said first end toward a longitudinal midsection of said sleeve, said first portion having a first inner circumference;

said sleeve having a second portion extending between said first portion and said second end, said second portion having a second inner circumference that is greater than said first circumference such that a radial and axial clearance exists between an end on the amputated limb and said second portion when the limb is received within said sleeve and wherein said second portion includes a radially defined opening for viewing the end of the amputated limb when the limb is received within said sleeve; and wherein said first portion includes a longitudinal split extending between said axial opening and said radially defined opening, said split allowing said first inner circumference to be adjusted independent of said second inner circumference.

13. The device of claim 12, wherein said second portion has a partially spherical shape.

14. The device of claim 12, wherein said longitudinal split defines a gap along said first portion, said gap having an adjustable dimension whereby said first inner circumference is adjustable.

15. The device of claim 14, further comprising an adjustable strap member for adjusting said gap dimension and maintaining said first inner circumference in a selected orientation about the amputated limb.

16. The device of claim 12, wherein said sleeve is formed of a copolymer substance such that said second portion is substantially rigid and said first portion is substantially rigid in an axial direction and generally flexible in a radial direction.

17. The device of claim 12, wherein said second portion has a fixed interior volume that is larger than an interior volume of said first portion.

18. A prosthetic device for use after a limb reduction surgery, comprising:

a generally cylindrical sleeve having an axial opening at a first end for receiving an amputated limb and having an axial closure at a second end distal from said axial opening;

said sleeve having a first portion extending from said axial opening toward a longitudinal midsection of said sleeve, said first portion including a longitudinal split extending along said first portion;

an adjustment member for adjusting a circumferential dimension of said first portion;

wherein said sleeve includes a second portion extending between said first portion and said second end, said second portion having a radially defined opening for viewing at least a terminal end on the amputated limb without removing the limb from said sleeve; and wherein said first portion has an inner surface circumference that is adjustable between a largest circumference and a smallest circumference by adjusting a spacing defined by said longitudinal split and wherein said second portion has an inner surface circumference that is greater than said largest first inner circumference.

19. A prosthetic device for use after an above-the-knee limb reduction surgery, comprising:

a generally cylindrical sleeve having an axial opening at a first end for receiving an amputated limb and being closed at a second axial end, said closed second end providing a load beating surface, which is adapted to be connected to a bendable knee joint, said first end including a load beating shelf portion adapted to bear against an ischial bone on a wearer of said device;

said sleeve having a first portion extending from said first end toward a longitudinal midsection of said sleeve, said first portion having an adjustable first inner circumference;

said sleeve having a generally spherical second portion extending between said first portion and said second end, said second portion having a fixed second inner surface circumference that is larger than said first circumference such that upon insertion, the amputated limb contacts only said first inner surface and a terminal end of the amputated limb does not contact said second inner surface of said second portion.

20. A prosthetic device for use after an above-the-knee limb reduction surgery, comprising:

a generally cylindrical sleeve having an axial opening at a first end for receiving an amputated limb and being closed at a second end distal from said axial opening, said second end providing a weight bearing surface;

a fixture supported on said second end that is adapted to be connected to a bendable knee joint;

said sleeve having a first portion extending from said axial opening toward a longitudinal midsection of said sleeve, said first portion including a longitudinal split extending along said first portion;

an adjustment member for adjusting a circumferential dimension of said first portion; and wherein said sleeve includes a second portion extending between said first portion and said second end, said second portion having a radially defined opening for viewing at least a terminal end on the amputated limb without removing the limb from said sleeve, wherein said first portion has an inner surface circumference that is adjustable between a largest circumference and a smallest circumference by adjusting the arcuate spacing defined by said longitudinal split and wherein said second portion has an inner surface circumference that is greater than said largest first inner circumference.

* * * * *